US006947135B2

(12) United States Patent
Johnson (10) Patent No.: US 6,947,135 B2
(45) Date of Patent: Sep. 20, 2005

(54) REDUCED MULTICUBIC DATABASE INTERPOLATION METHOD FOR OPTICAL MEASUREMENT OF DIFFRACTIVE MICROSTRUCTURES

(75) Inventor: Kenneth C. Johnson, Santa Clara, CA (US)

(73) Assignee: Therma-Wave, Inc., Fremont, CA (US)

(*) Notice: Subject to any disclaimer, the term of this patent is extended or adjusted under 35 U.S.C. 154(b) by 236 days.

(21) Appl. No.: 10/611,298

(22) Filed: Jul. 1, 2003

(65) Prior Publication Data

US 2004/0032582 A1 Feb. 19, 2004

Related U.S. Application Data

(60) Provisional application No. 60/426,602, filed on Nov. 15, 2002, and provisional application No. 60/392,953, filed on Jul. 1, 2002.

(51) Int. Cl.[7] .................... G01N 21/88; G01B 11/06
(52) U.S. Cl. ............. 356/327.2; 702/155; 702/179; 702/23; 382/300
(58) Field of Search .......................... 356/237.1–237.6, 356/600–601, 625, 446; 250/339.11, 339.08; 382/300, 245, 263; 702/179, 23, 32–35, 40

(56) References Cited

U.S. PATENT DOCUMENTS

| | | | | |
|---|---|---|---|---|
| 5,607,800 A | * | 3/1997 | Ziger ............................. | 430/8 |
| 5,867,276 A | | 2/1999 | McNeil et al. ............... | 356/445 |
| 5,905,822 A | * | 5/1999 | Ito et al. ...................... | 382/300 |
| 6,242,739 B1 | * | 6/2001 | Cherkassky ............ | 250/339.11 |
| 6,476,920 B1 | * | 11/2002 | Scheiner et al. ............ | 356/630 |
| 6,590,656 B2 | | 7/2003 | Xu et al. ..................... | 356/369 |
| 6,768,976 B1 | * | 7/2004 | Homma et al. ............... | 703/14 |
| 6,867,866 B1 | * | 3/2005 | Chang et al. ............... | 356/446 |
| 2002/0038196 A1 | | 3/2002 | Johnson et al. ............. | 702/179 |

OTHER PUBLICATIONS

G.H. Schut, "Review of Interpolation Methods for Digital Terrain Models," *The Canadian Surveyor*, vol. 30, No. 5, Dec. 1976, pp. 389–412.
W.S. Russell, "Polynomial interpolation schemes for internal derivative distributions on structured grids," *Applied Numerical Mathematics*, vol. 17, 1995, pp. 129–171.
W.H. Press et al., *Numerical Recipes in C++* (*The Art of Scientific Computing*), 2nd Edition, Cambridge University Press, Chapter 3, "3.6 Interpolation in Two or More Dimensions," 2002, pp. cover page, 126–132.
D. Kidner et al., "What's the point? Interpolation and extrapolation with a regular grid DEM," *Proceed. 4th Internat. Conf. on Geocomputation* (Fredericksburg, VA), Jul. 25–29, 1999, 17 pages in length.

* cited by examiner

*Primary Examiner*—Gregory J. Toatley, Jr.
*Assistant Examiner*—Sang H. Nguyen
(74) *Attorney, Agent, or Firm*—Stallman & Pollock LLP (57) ABSTRACT

A reduced multicubic database interpolation method is provided. The interpolation method is designed to map a function and its associated argument into an interpolated value using a database of points. The database is searched to locate an interpolation cell that includes the function argument. The interpolation cell is used to transform the function argument to reflect translation of the interpolation cell to a unit cell. The interpolated value is then generated as a cubic function using the data points that correspond to vertices of the unit cell. All of the derivatives in the cubic function are simple and the interpolation accuracy order is higher than first-order.

13 Claims, 2 Drawing Sheets

REDUCED MULTICUBIC DATABASE INTERPOLATION METHOD FOR OPTICAL MEASUREMENT OF DIFFRACTIVE MICROSTRUCTURES

PRIORITY CLAIM

The present application claims priority to U.S. Provisional Patent Application Ser. No. 60/392,953, filed Jul. 1, 2002 and U.S. Provisional Patent Application Ser. No. 60/426,602, filed Nov. 15, 2002. The disclosure of both of these documents is incorporated herein by reference.

TECHNICAL FIELD

The subject invention relates generally to optical methods for inspecting and analyzing semiconductor wafers and other samples. In particular, the subject invention relates to improvements in analysis of the measured optical signal characteristics from a sample to determine parameter values for that sample.

BACKGROUND OF THE INVENTION

As geometries continue to shrink, manufacturers have increasingly turned to optical techniques to perform non-destructive inspection and analysis of semiconductor wafers. Techniques of this type, known generally as optical metrology, operate by illuminating a sample with electromagnetic radiation and then detecting and analyzing the reflected energy. Scatterometry is a specific type of optical metrology that is used when the structural geometry of a subject creates diffraction (optical scattering) of the incoming probe beam. Scatterometry systems analyze diffraction to deduce details of the structures that cause the diffraction to occur. In general, optical metrology measures physical dimensions and/or material properties of structures on a wafer from the optical response of the wafer, that is, how the wafer changes light that illuminates it.

Various optical techniques have been used to perform optical scatterometry. These include broadband spectroscopy (U.S. Pat. Nos. 5,607,800; 5,867,276 and 5,963,329), spectral ellipsometry (U.S. Pat. No. 5,739,909) single-wavelength optical scattering (U.S. Pat. No. 5,889,593), and spectral and single-wavelength beam profile reflectance and beam profile ellipsometry (U.S. Pat. No. 6,429,943). Scatterometry, in these cases generally refers to optical responses in the form of diffraction orders produced by period structures, that is, gratings on the wafer. In addition it may be possible to employ any of these measurement technologies, e.g., single-wavelength laser BPR or BPE, to obtain critical dimension (CD) measurements on non periodic structures, such as isolated lines or isolated vias and mesas. The above cited patents and patent applications, along with PCT Application WO03/009063, U.S. application Ser. No. 2002/0158193, U.S. application Ser. No. 10/243245, filed Sep. 13, 2002, U.S. application Ser. No. 2001/0051856 A1, PCT Application WO 01/55669 and PCT Application WO 01/97280 are all incorporated herein by reference.

Metrology uses three classes of parameters and their relationships. Structures on the wafer have physical parameters, e.g., the thickness of a layer, the widths of a line structure at various heights (measured generally perpendicular to a face of the wafer, or the complex optical index of a material. Most scatterometry measurements are performed over a range of independent parameters. Examples independent parameters are wavelength (for spectroscopic systems) or angle of propagation. Much of the following is written as if wavelength is the independent parameter. The goal of metrology is to relate measurements to a model of what is on the wafer, where the model has parameters that in some sense reflect the physical parameters on the wafer. In some cases, model parameters represent exactly the physical parameters in question, or they may be related through some mathematical transformation, e.g., the physical widths of adjacent periodic lines and spaces may be modeled as a period and ratio.

Most scatterometry systems use a modeling approach to transform empirical data into tangible results. For this type of approach, a theoretical model is defined for each subject that will be analyzed. The theoretical model predicts the output (reflected) electromagnetic field that is generated when an incident field is applied to the subject. The theoretical model is parameterized and each parameter corresponds to a physical characteristic of the subject such as line width or layer thickness. A profile is a collection of line widths at various heights, and is thus a collection of parameters. A regression is performed in which the parameters are repeatedly perturbed and the model is repeatedly evaluated to minimize the differences between the modeled results and results that are empirically obtained. The differences are typically calculated over the range of the independent parameters, and then an average difference, such as a squared sum, is calculated as a single difference. Various norms or other techniques are suitable for collapsing the multiple differences into a single working difference. When the minimization reaches some stopping criterion, it is assumed that the model and its associated parameters accurately reflect the subject being analyzed. One such stopping criterion is that the difference reaches some predetermined level, e.g., that a goodness-of-fit criterion is exceeded. Another criterion is reached when the reduction of the difference from repeat to repeat becomes sufficiently small. Others are possible.

Evaluation of theoretical scatterometry models is a complex task, even for relatively simple subject. As subjects become more complex, e.g., having more parameters, the calculations can become extremely time-consuming. Even with high-speed processors, real-time evaluation of these calculations can be difficult. This is problematic in semiconductor manufacturing where it is often imperative to detect processes that are not operating correctly. As the semiconductor industry moves towards integrated metrology solutions (i.e., where metrology hardware is integrated directly with process hardware) the need for rapid evaluation becomes even more acute.

A number of approaches have been developed to overcome the calculation bottleneck associated with the analysis of scatterometry results. Many of these approaches have involved techniques for improving calculation throughput, such as parallel processing techniques. For example, co-pending application Ser. No. 09/906,290 filed Jul. 16, 2001 describes a system in which a master processor distributes scatterometry calculations among a group of slave processors. This can be done by as a function of wavelength, so that each slave processor evaluates the theoretical model for selected wavelengths. The other slave processors will carry out the same calculations at different wavelengths. Assuming there are five processors (one master and four slaves) and fifty wavelengths, each processor will perform ten such calculations per iteration. Once complete, the master processor combines the separate calculation and performs the best fit comparison to the empirical results. Based on this fit, the master processor will modify the parameters of the model (e.g. changing the widths or layer thickness) and distribute the calculations for the modified model to the slave processors. This sequence is repeated until a good fit is achieved.

This distributed processing approach can also be used with multiple angle of incidence information. In this situation, the calculations at each of the different angles of incidence can be distributed to the slave processor. Techniques of this type are an effective method for reducing the time required for scatterometry calculations. At the same time, the speedup provided by parallel processing is strictly dependent on the availability (and associated cost) of multiple processors. Amdahl's law also limits the amount of speedup available by parallel processing since serial portions of the program are not improved. At the present time, neither cost nor ultimate speed improvement is a serious limitation for parallel processing techniques. As the complexity of the geometry increases, however it becomes increasingly possible that computational complexity will outstrip the use of parallel techniques alone.

Another approach to rapidly evaluating scatterometry measurements is to use pre-computed libraries of predicted measurements. This type of approach is discussed in PCT application WO 99/45340, published Sep. 10, 1999 as well as the references cited therein. In this approach, a library of expected results is constructed by repeatedly evaluating the theoretical model for range of different parameters. When empirical measurements are obtained, the library is searched to find the best fit.

The use of libraries speeds the analysis process by allowing theoretical results to be computed once and reused many times. Of course, libraries are necessarily limited in their resolution and can contain only a finite number of theoretical results. This means that there are many cases where empirical measurements do not have exact library matches. In these cases, the use of a library represents an undesirable choice between speed and computational accuracy.

To overcome this limitation, U.S. Patent Application Publication No. 20020038196A1 (incorporated in this document by reference) describes a database method of analysis of empirical scatterometry measurements. The database method is similar to the library approach in that it relies on a stored set of pre-computed "reflectance characteristics." (The reflectance characteristics could be simulated reflectance signal spectra, although in the preferred embodiment they are complex reflectance coefficients from which the reflectance signal can be computed without resorting to complex electromagnetic simulations). In this case, however an interpolation method is used in combination with the database-stored characteristics, making it possible to achieve measurement resolution and accuracy much better than the database sampling resolution. Both the database size and computation time are consequently greatly reduced relative to library-based methods.

A critical element of the database interpolation method is the interpolation algorithm itself. In the application just cited (i.e., U.S. Patent Application Publication No.20020038196A1), two preferred algorithms are disclosed: multilinear and multicubic. Multilinear interpolation is very fast, but has poor accuracy. Multicubic interpolation is much more accurate, but can be slow, especially when many parameters are being simultaneously measured. In practice, selection of between multilinear and multicubic method is done on a pragmatic basis depending on the degree of accuracy and speed required. Often, this choice is totally acceptable. This is true, for example, when the number of parameters is relatively small. Still, it is clear that interpolation methods that provide increased speed and accuracy would be an improvement over current techniques.

SUMMARY

An embodiment of the present invention provides an interpolation method for analyzing empirical scatterometry measurements. The interpolation method is a variant type of cubic interpolation algorithm that exhibits very good accuracy—comparable to multicubic—but which has much better runtime performance (e.g. for one particular example the runtime for a six-parameter measurement was reduced from 6.5 sec to 1.9 sec).

The objective of the interpolation algorithm is to estimate values of a reflectance characteristic function:

$$f[x_0, x_1, \ldots, x_{N-1}]$$

wherein the x's are measurement parameters (e.g., film thicknesses, grating linewidths, etc.). The estimate is obtained from a set of pre-computed function values sampled on a rectangular grid in an N-dimensional "parameter space." The reflectance characteristic function $f[x_0, x_1, \ldots, x_{N-1}]$ is approximated as a linear combination of function values selected from the precomputed set, wherein the specific set of selected values and associated linear combination coefficients are determined from the parameter values $x_0, x_1, \ldots$ . The interpolation method requires $(N+1)2^N$ sample points per interpolation (e.g.: 448 for six parameters). This is comparable to multilinear interpolation which uses $2^N$ sample points (e.g.: 64 sample points for six parameters) and much better than multicubic interpolation which requires $4^N$ sample points (e.g.: 4096 sample points for six parameters).

The essence of the improved method can be summarized as follows: The reflectance characteristic function $f[x_0, x_1, \ldots, x_{N-1}]$ is approximated as a polynomial function of $x_0, x_1, \ldots$ consisting of a linear combination of elemental monomial functions. The monomial terms include all of the multilinear monomials, $$x_0^{p_0} x_1^{p_1} \ldots$$

wherein each of the exponents $p_0, p_1, \ldots$ is either 0 or 1. (There are $2^N$ such terms.) The monomials also include the multilinear terms multiplied by the square: of any one of the parameters, $$(x_0^{p_0} \; x_1^{p_1} \; \cdots) x_0^2$$
$$(x_0^{p_0} \; x_1^{p_1} \; \cdots) x_1^2$$
$$\ldots$$

Including all such terms, the total number of monomials making up the polynomial interpolation function is: $(N+1)2^N$. The same number of conditions is required to determine the polynomial coefficients. These conditions are determined by specifying the function values and its gradient at the corners of an N-dimensional box (a database "grid cell") enclosing the interpolation point $\{x_0, x_1, \ldots\}$. (If the interpolation point is outside of the database sampling range there will be no grid cell enclosing the interpolation point. In this case the grid cell nearest the interpolation point may be used to extrapolate the function outside the database range.) The gradient values may be obtained by either storing gradient information in the database or by applying a finite-difference derivative estimator to the database-sampled function values. In either case, the number of database quantities (function values and possible derivative values) required to determine the polynomial coefficients is $(N+1)2^N$.

The reduced multicubic interpolation function is:

$$f[x_0, x_1, \ldots, x_{N-1}] = \sum_{j_0, j_1, \ldots \in \{0,1\}} \left( a_{j_0, j_1, \ldots} + \sum_{k \in \{0,1,\ldots,N-1\}} b_{k;j_0,j_1,\ldots} x_k^2 \right) x_0^{j_0} x_1^{j_1} \ldots$$

$$0 \le x_m \le 1$$

With the boundary constraints:

$$f[j_0, j_1, \ldots] = f_{j_0, j_1, \ldots};$$

$$\frac{\partial}{\partial j_k} f[j_0, j_1, \ldots] = df_{k;j_0,j_1,\ldots}; j_m \in \{0, 1\}$$

The right-hand sides of the constraint equations are predetermined values. (Number of unknown a and b coefficients=number of constraints=$(N+1)2^N$.) Implicit solution for the a and b coefficients in terms of interpolation basis functions (U and V):

$$f[x_0, x_1, \ldots] = \sum_{j_0, j_1, \ldots} f_{j_0, j_1, \ldots} U_{j_0, j_1, \ldots} [x_0, x_1, \ldots] + \sum_{k, j_0, j_1, \ldots} df_{k;j_0,j_1,\ldots} V_{k;j_0,j_1,\ldots} [x_0, x_1, \ldots]$$

The basis functions have the same functional form as $f$ and satisfy the defining conditions.

For $x_0, x_1, \ldots = 0$ or $1$:

$$U_{j_0, j_1, \ldots} [x_0, x_1, \ldots] = 0, \text{ except } U_{j_0, j_1, \ldots} [j_0, j_1, \ldots] = 1$$

$$\frac{\partial}{\partial x_m} U_{j_0, j_1, \ldots} [x_0, x_1, \ldots] = 0$$

$$V_{k;j_0,j_1,\ldots} [x_0, x_1, \ldots] = 0$$

$$\frac{\partial}{\partial x_m} V_{k;j_0,j_1,\ldots} [x_0, x_1, \ldots] = 0,$$

$$\text{except } \frac{\partial}{\partial x_k} V_{k;j_0,j_1,\ldots} [j_0, j_1, \ldots] = 1$$

The following defining relations for U and V satisfy the above conditions:

$$U_{0,0,\ldots} [x_0, x_1, \ldots] = (1-x_0)(1-x_1) \ldots (1+x_0(1-2x_0) + x_1(1-2x_1) + \ldots)$$

$$U_{j_0, j_1, \ldots} [x_0, x_1, \ldots]|_{j_m \to 1-j_m} = U_{j_0, j_1, \ldots} [x_0, x_1, \ldots]|_{x_m \to 1-x_m}$$

$$V_{0;0,0,\ldots} [x_0, x_1, \ldots] = x_0(1-x_0)^2(1-x_1)(1-x_2) \ldots$$

$$V_{k;0,0,\ldots} [x_0, x_1, \ldots] = V_{0;0,0,\ldots} [x_0, x_1, \ldots]|_{x_0 \to x_k, x_k \to x_0}$$

$$m \ne k: V_{k;j_0,j_1,\ldots} [x_0, x_1, \ldots]|_{j_m \to 1-j_m} = V_{k;j_0,j_1,\ldots} [x_0, x_1, \ldots]|_{x_m \to 1-x_m}$$

$$V_{k;j_0,j_1,\ldots} [x_0, x_1, \ldots]|_{j_k \to 1-j_k} = -V_{k;j_0,j_1,\ldots} [x_0, x_1, \ldots]|_{x_k \to 1-x_k}$$

Combining the above conditions, the following result is obtained:

$$U_{j_0, j_1, \ldots} [x_0, x_1, \ldots] = (1-x'_0)(1-x'_1) \ldots (1+x'_0(1-2x'_0) + x'_1(1-2x'_1) + \ldots)$$

and:

$$V_{k;j_0,j_1,\ldots} [x_0, x_1, \ldots] = (-1)^{j_k} x'_k (1-x'_k)(1-x'_0)(1-x'_1)(1-x'_2) \ldots$$

wherein:

$$x'_m = \begin{cases} x_m, & j_m = 0 \\ 1 - x_m, & j_m = 1 \end{cases}$$

As noted above, the interpolation method dramatically reduces the number of values that must be used during the interpolation step associated with computing the reflectance characteristics of a sample. For example, the number of values necessary to perform this interpolation when applied to a database wherein each point is defined by six parameters is only about one-tenth of the number of values needed with the multicubic approach. This computational savings increases for higher parameter problems (e.g.: with a seven parameter problem, the number of values needed for the interpolation is only one-sixteenth of the values needed for the multicubic approach). Although number of values used for the interpolation is reduced, the interpolation method nonetheless produces interpolation results that fit all data points, with a smooth curve between data points and a smooth transition around data points. In addition to analyzing measured data, the interpolation method can also be used to reduce the complexity and time needed to generate a database.

DETAILED DESCRIPTION OF THE PREFERRED EMBODIMENTS

The present invention provides several related reduced multicubic interpolation methods. Each of these methods is specifically intended to be used during the analysis of empirical scatterometry measurements. At the same time, it should be appreciated that a diverse range of other applications are also possible, including digital terrain mapping and color interpolation for computer graphics.

Figure 1:
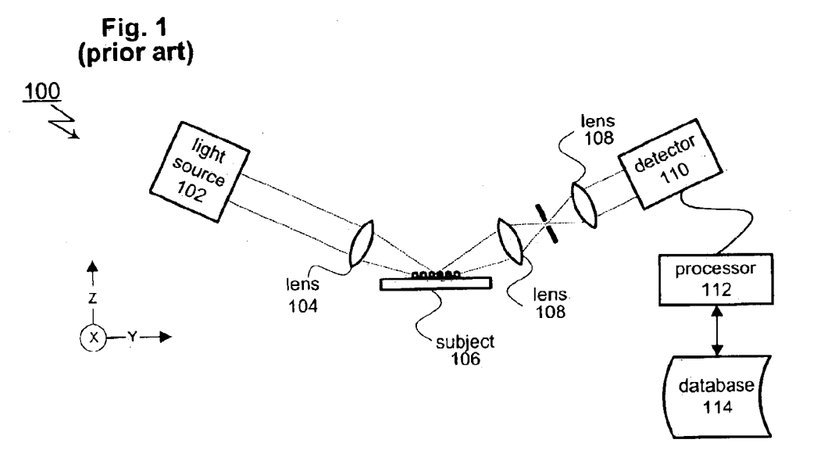
FIG. 1 is a diagram of a prior art optical metrology system.

FIG. 1 shows a scatterometer of a type suitable for use with the reduced multicubic interpolation method. As shown in FIG. 1, scatterometer 100 includes an illumination source 102 that creates a mono or polychromatic probe beam. The probe beam is preferably focused by one or more lenses 104 to create an illumination spot on the surface of the subject under test 106. A second lens (or lenses) 108 transports the diffracted probe beam to a detector 110. Detector 110 captures the diffracted energy and produces corresponding output signals. A processor 112 analyzes the signals generated by detector 110 using a database 114.

Figure 2:
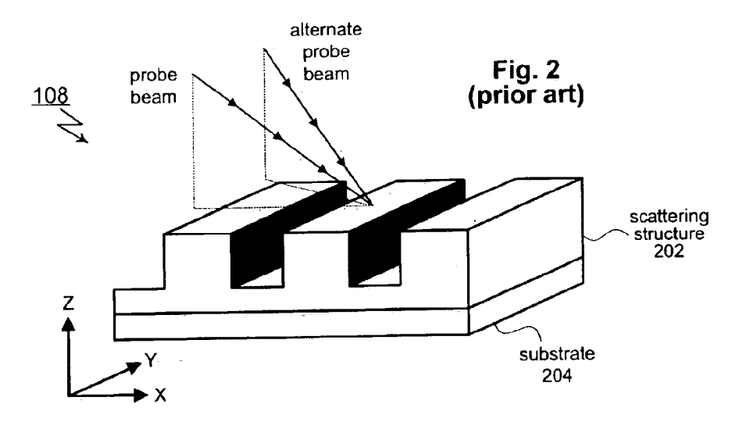
FIG. 2 is a perspective drawing of a typical scatterometry subject.

As shown in FIG. 2, scatterometry subject 106 typically includes a scattering structure 202 formed on a substrate 204. For the specific example of FIG. 2, the scattering structure is a grating composed of a series of individual lines. In general, the scattering structure may be periodic (as in the case of FIG. 2) or isolated. Isolated structures include, for example individual lines, or individual vias. The scattering structure of FIG. 2 is uniform (i.e., exhibits translational symmetry) along the Y axis. For this reason, this particular scattering structure is considered to be two-dimensional. Three dimensional scattering structures are also possible both in isolation (e.g., a single via) or periodically (e.g., a pattern of vias). The scatting structure is covered by an incident medium that is typically air but may be vacuum, gas, liquid, or solid (such as an overlaying layer or layers). One or more layers may be positioned between the scattering structure and the substrate. Alternatively, more than one layer may have a scattering structure, as is described in U.S. Patent Application Publication Number: 20020158193 (incorporated in this document by reference). During analysis, a probe beam is directed at the scattering structure. For most applications, the probe beam intersects the scattering structure at a normal azimuthal angle—the propagation vector is in the plane perpendicular to the lines from which the scattering structure is formed. It is also possible to use a non-normal azimuthal angle. This is referred to as conical scattering.

The relationship between the incoming and diffracted probe beam is controlled by the optical response characteristics of subject 106. To analyze the empirical measurements made by scatterometer 100 (i.e., the empirical optical response characteristics) a modeling process is typically used. The modeling process is based on a parametric model of the particular subject being analyzed (e.g, Lifeng Li, "A modal analysis of lamellar diffraction gratings in conical mountings", Journal of Modern Optics, 1993, Vol. 40, No. 4, 553–573). The model is evaluated to compute predicted or theoretical optical response characteristics for the subject. The theoretical and empirical optical response characteristics are compared to determine if the model matches the empirical results. The model is then perturbed (i.e., the parameters are varied) and re-evaluated until the theoretical results and empirical results match within a desired goodness of fit. At that point, the parametric model is assumed to match the subject being analyzed.

Database 114 is constructed to include a series of pre-computed theoretical optical response characteristics. Each of these theoretical optical response characteristics is stored in association with its corresponding modeling parameters to define an interpolation point within database 114. Typically, each stored optical response characteristic includes a series of complex reflectance coefficients or scattering matrices associated with different illumination wavelengths, incidence directions, and polarization states, but all associated with the same diffractive structure configuration (materials and geometry). The computational representation of the associated structure geometry (e.g., profile shape) is not required for subsequent measurement processes and need not be stored in the database.

Database 114 is necessarily limited to include a finite number of interpolation points. The reduced multicubic interpolation methods provided by the present invention provide a mechanism for accurately interpolating optical response characteristics that fall between interpolation points within database 114 (or in some cases are outside of the limits of database 114). This makes database 114 appear to have an infinite number of interpolation points without requiring that the theoretical model be reevaluated for each optical response characteristic that is not specifically associated with an existing interpolation point.

In this document, interpolation (including the reduced multicubic interpolation methods provided by the present invention) is described in terms of a function Y[X]. For scatterometry, Y[X] is the function that is used to generate theoretical optical response characteristics. The interpolation points in database 114 are evaluations of Y[X] stored in combination with the corresponding values of X. The output of Y[X] is typically a vector or matrix that typically includes (e.g., for the case of scatterometry) computed reflectance quantities such as complex reflectance corresponding to multiple wavelengths, incidence angles, and polarization states. The input to Y[X] is typically an N-dimensional, vector argument $X=(X_1, X_2, \ldots X_N)$ (For clarity square braces [ ... ] are used as function argument delimiters and round braces ( ... ) are reserved for grouping; vectors and matrices are represented in bold type).

In the preferred embodiment, Y[X] is sampled at the points of a rectangular grid on which each $X_j$ takes on the discrete values $$X_j = X_j^{(0)}, X_j^{(1)}, \ldots X_j^{(M_j)}; \; j=1 \ldots N \tag{1}$$

(The $X_j$ sampling values are sorted in increasing order: $X_j^{(0)} < X_j^{(1)} < \ldots X_j^{(M_j)}$.)

Some interpolation algorithms require a specification of not just Y, but also some set of partial derivatives of Y at the grid points. In this document, the j-th partial derivative operator is denoted $\partial_j$, and product notation is used to denote derivative operator composition as follows:

$$\partial_j^k Y[(X_1, X_2, \ldots X_N)] = \frac{\partial^k}{\partial X_j^k} Y[(X_1, X_2, \ldots X_N)] \tag{2}$$

$$\left( \prod_{j=1,2,\ldots} \partial_j^{k_j} \right) Y = \partial_1^{k_1} \partial_2^{k_2} \ldots Y$$

(Note: for k=0, $\partial_j^k Y = Y$).

The grid sampling-point vectors are denoted as:

$$X^{(m)} = (X_1^{(m_1)}, X_2^{(m_2)}, \ldots X_N^{(m_N)}); \; m_j=0 \ldots M_j; \; j=1 \ldots N \tag{3}$$

wherein m is a "grid index vector", $m=(m_1, m_2, \ldots m_N)$. The interpolation domain is partitioned into N-dimensional, rectangular "grid cells" with cell vertices at the grid points. For a grid index vector m, "cell m" denotes a grid cell defined by the constraints $X_j^{(m_j)} \leq X_j \leq X_j^{(m_j+1)}$ ($X^{(m)}$ is the "base vertex" of cell m). Within cell m, Y[X] is approximated by an interpolation function $Y_1^{(m)}[X]$:

$$Y[X] \approx Y_1^{(m)}[X]; \; X_j^{(m_j)} \leq X_j \leq X_j^{(m_j+1)}; \; m_j=0 \ldots M_j-1; \; j=1 \ldots N \tag{4}$$

The collection of cell-bounded interpolation functions $Y_1^{(m)}[X]$ defines a global interpolation function $Y_1[X]$ over the entire interpolation domain ($X_j^{(0)} \leq X_j \leq X_j^{(M_j)}$).

The computation of $Y_1^{(m)}$ is simplified by applying a linear transformation to X in order to transform grid cell m into a unit cell with its base vertex at the origin. The transformed X argument, denoted $x=(x_1, x_2, \ldots x_N)$, is defined by $$x_j = \frac{X_j - X_j^{(m_j)}}{X_j^{(m_j+1)} - X_j^{(m_j)}}; \; j = 1 \ldots N \tag{5}$$

The functions Y and $Y_1^{(m)}$ translate to transformed functions y and $y_1$, $$y[x] = Y[X], \; y_1[x] = Y_1^{(m)}[X] \tag{6}$$

The Y derivatives transform as follows, $$\partial_j y[x] = (X_j^{(m_j+1)} - X_j^{(m_j)}) \partial_j Y[X] \tag{7}$$

(and similarly for $Y_1$).

The vertices of cell m are at $X=X^{(m+s)}$; wherein s is the integer vector $s=(s_1, s_2, \ldots s_N)$ with element values 0 or 1: $s_j=0,1$; $j=1 \ldots N$. The Equation 5 transformation maps $X=X^{(m+s)}$ onto $x=s$; thus the problem is to find an interpolating function $y_1[x]$ approximating $y[x]$ within the interpolation cell $0 \leq x_j \leq 1$ ($j=1 \ldots N$), given a sampling of y and (possibly) some set of its derivatives at the cell vertices $x=s$; $s_j=0,1$. (In some interpolation algorithms, finite-difference derivatives are employed using some external y points sampled outside of the interpolation cell. In this case it may be necessary to "pad" the data sampling range with points outside the interpolation range to cover these external points.)

Multilinear Interpolation

This section describes a prior art multilinear interpolation technique. This technique is presented because it provides a relatively simple example of the nomenclature and formalisms just described. The description of multilinear interpolation is also important in later sections which evaluate the performance of the interpolation methods provided by the present invention. Multilinear interpolation provides an interpolation function $y_1[s]$ that matches the function being interpolated at each grid point of s:

$$y_1[s] = y[s]; \quad s_j=0,1; \quad j=1 \ldots N \tag{8}$$

The interpolation function has the form:

$$y_I[x] = \sum_{s: s_j=0,1 (j=1 \ldots N)} u_s[x] y[s] \tag{9}$$

The $u_s[x]$ factors are "interpolation basis functions" defined by:

$$u_s[x] = \prod_{j=1 \ldots N} (1 - x'_j) \tag{10}$$

in which $x'_j$ is shorthand for:

$$x'_j = \begin{cases} x_j, & s_j = 0 \\ 1 - x_j, & s_j = 1 \end{cases} \tag{11}$$

Multicubic Interpolation

This section describes the prior art multicubic interpolation technique. This technique is presented (once again) as a relatively simple example of the nomenclature and formalisms used throughout this description. The description of multicubic interpolation is also important in later sections which evaluate the performance of the interpolation methods provided by the present invention. Like the multilinear interpolation function, the prior art multicubic interpolation function $y_1$ matches y at the grid points s. In addition, the first-order derivatives ($\partial_1 y_1, \partial_2 y_1$, etc.), and mixed-first-order derivatives ($\partial_1 \partial_2 y_1, \partial_1 \partial_2 \partial_3 y_1$, etc.) of $y_1$ also match y at the grid points s:

$$\left(\prod_{j=1 \ldots N} \partial_j^{k_j}\right) y_I[s] = \left(\prod_{j=1 \ldots N} \partial_j^{k_j}\right) y[s]; \tag{12}$$

$$k_j = 0, 1; s_j = 0, 1; j = 1 \ldots N$$

The interpolation function is $$y_I[x] = \sum_{k: k_j=0,1 (j=1 \ldots N)} \sum_{s: s_j=0,1 (j=1 \ldots N)} u_{k,s}[x] \left(\prod_{j=1 \ldots N} \partial_j^{k_j}\right) y[s] \tag{13}$$

wherein $k=(k_1, k_2, \ldots k_N)$. The interpolation basis functions, $u_{k,s}[x]$, are defined by $$u_{k,s}[x] = \prod_{j=1 \ldots N} (-1)^{k_j s_j} f_{k_j}[x'_j] \tag{14}$$

in which $$f_{k_j}[x_j] = \begin{cases} (1-x_j)^2 (1+2x_j), & k_j = 0 \\ (1-x_j)^2 x_j, & k_j = 1 \end{cases} \tag{15}$$

and $x'_j$ is defined as:

$$x'_j = \begin{cases} x_j, & s_j = 0 \\ 1 - x_j, & s_j = 1. \end{cases}$$

Reduced-Cubic Interpolation with Exact Derivatives

As provided by the present invention, reduced-cubic interpolation matches $y_1$ and its simple derivatives to y at the grid points s (in this document, the term simple derivative refers to derivatives that are first order and are not mixed-partial derivatives—e.g., $\partial_1 y_1$ and $\partial_2 y_1$ but not $\partial_1 \partial_2 y_1$ or $\partial_1^2 y_1$):

$$y_1[s] = y[s], \partial_i y_1[s] = \partial_i y[s]; s_j=0,1; i,j=1 \ldots N \tag{16}$$

The interpolation function is:

$$y_I[x] = \sum_{s: s_j=0,1 (j=1 \ldots N)} \left(u_s[x] y[s] + \sum_{i=1 \ldots N} v_{i,s}[x] \partial_i y[s]\right) \tag{17}$$

The interpolation basis functions, $u_s[x]$ and $v_{i,s}[x]$, are defined by:

$$u_s[x] = \left(\prod_{j=1 \ldots N} (1 - x'_j)\right)\left(1 + \sum_{j=1 \ldots N} x'_j(1 - 2x'_j)\right) \tag{18}$$

$$v_{i,s}[x] = (-1)^{s_i} \left(\prod_{j=1 \ldots N} (1 - x'_j)\right) x'_i(1 - x'_i)$$

and $x'_j$ is defined as:

$$x'_j = \begin{cases} x_j, & s_j = 0 \\ 1 - x_j, & s_j = 1. \end{cases}$$

As an example, consider the one dimensional case (i.e., $N=1$). For this case, the interpolation function is:

$$y_1[x] = u_0[x] y[0] + v_{1,0}[x] \partial y[0] + u_1[x] y[1] + v_{1,1}[x] \partial y[1]$$

and the interpolation basis functions are:

$$u_0[x] = (1 - 3x_1^2 + 2x_1^3) u_1[x] = (x_1^2)(3 - 2x_1)$$

$$v_{1,0}[x] = (1-x_1)^2 x_1 v_{1,1}[x] = (-1)(x_1)^2(1-x_1)$$

which gives:

$$y_1[x] = (1 - 3x_1^2 + 2x_1^3) y[0] + x_1^2(3 - 2x_1) y[1] + x_1(1-x_1)^2 \partial y[0] - x_1^2(1-x_1) \partial y[1]$$

Similarly, for the two dimensional case (i.e., N=2), the interpolation function is:

$$y_I[x_1, x_2] = \sum_{s_1,s_2=0,1} (u_{s_1,s_2}[x_1, x_2]y[s_1, s_2] + v_{1,s_1,s_2}[x_1, x_2]\partial_1 y[s_1, s_2] + v_{2,s_1,s_2}[x_1, x_2]\partial_2 y[s_1, s_2])$$

or:

$u_{0,0}[x_1,x_2]y[0,0]+v_{1,0,0}[x_1,x_2]\partial_1 y[0,0]+v$ $2,0,0[x_1,x_2]\partial_2 y[0,0]+u_{0,1}[x_1,x_2]y[0,1]+v_{1,0,1}[$ $x_1,x_2]\partial_1 y[0,1]+v_{2,0,1}[x_1,x_2]\partial_2 y[0,1]+u_{1,0}[$ $x_1,x_2]y[1,0]+v_{1,1,0}[x_1,x_2]\partial_1 y[1,0]+v_{2,1,0}[x_1,x$ $2]\partial_2 y[1,0]+u_{1,1}[x_1,x_2]y[1,1]+v_{1,1,1}[x_1,x_2]$ $\partial_1 y[1,1]+v_{2,1,1}[x_1,x_2]\partial_2 y[1,1]$ and the interpolation basis functions are:

$u_{s_1,s_2}[x_1,x_2]=(1-x'_1)(1-x'_2)(1+x'_1(1-2x'_1)x'_2(1-2x'_2))$ and:

$v_{i,s_1,s_2}[x_1,x_2]=(-1)^{s_i}(1-x'_1)(1-x'_2)x'_i(1-x'_i)$ which expand to:

$u_{0,0}[x_1,x_2]=(1-x_1)(1-x_2)(1+x_1(1-2x_1)x_2(1-2x_2))$ $u_{0,1}[x_1,x_2]=(1-x_1)(x_2(1+x_1(1-2x_1)(1-x_2)(2x_2-1))$ $u_{1,0}[x_1,x_2]=x_1(1-x_2)(1+(1-x_1)(2x_1-1)x_2(1-2x_2))$ $u_{1,1}[x_1,x_2]=x_1x_2(1+(1-x_1)(2x_1-1)(1-x_2)(2x_2-1))$ and:

$v_{1,0,0}[x_1,x_2]=(1-x_1)(1-x_2)x_1(1-x_1)$ $v_{1,0,1}[x_1,x_2]=(1-x_1)(x_2x_1(1-x_1)$ $v_{1,1,0}[x_1,x_2]=-x_1(1-x_2)(1-x_1)x_1$ $v_{1,1,1}[x_1,x_2]=-x_1x_2(1-x_1)x_1$ $v_{2,0,0}[x_1,x_2]=(1-x_1)(1-x_2)x_2(1-x_2)$ $v_{2,0,1}[x_1,x_2]=-(1-x_1)x_2(1-x_2)x_2$ $v_{2,1,0}[x_1,x_2]=x_1(1-x_2)x_2(1-x_2)$ $v_{2,1,1}[x_1,x_2]=-x_1x_2(1-x_2)x_2$

Figure 3:
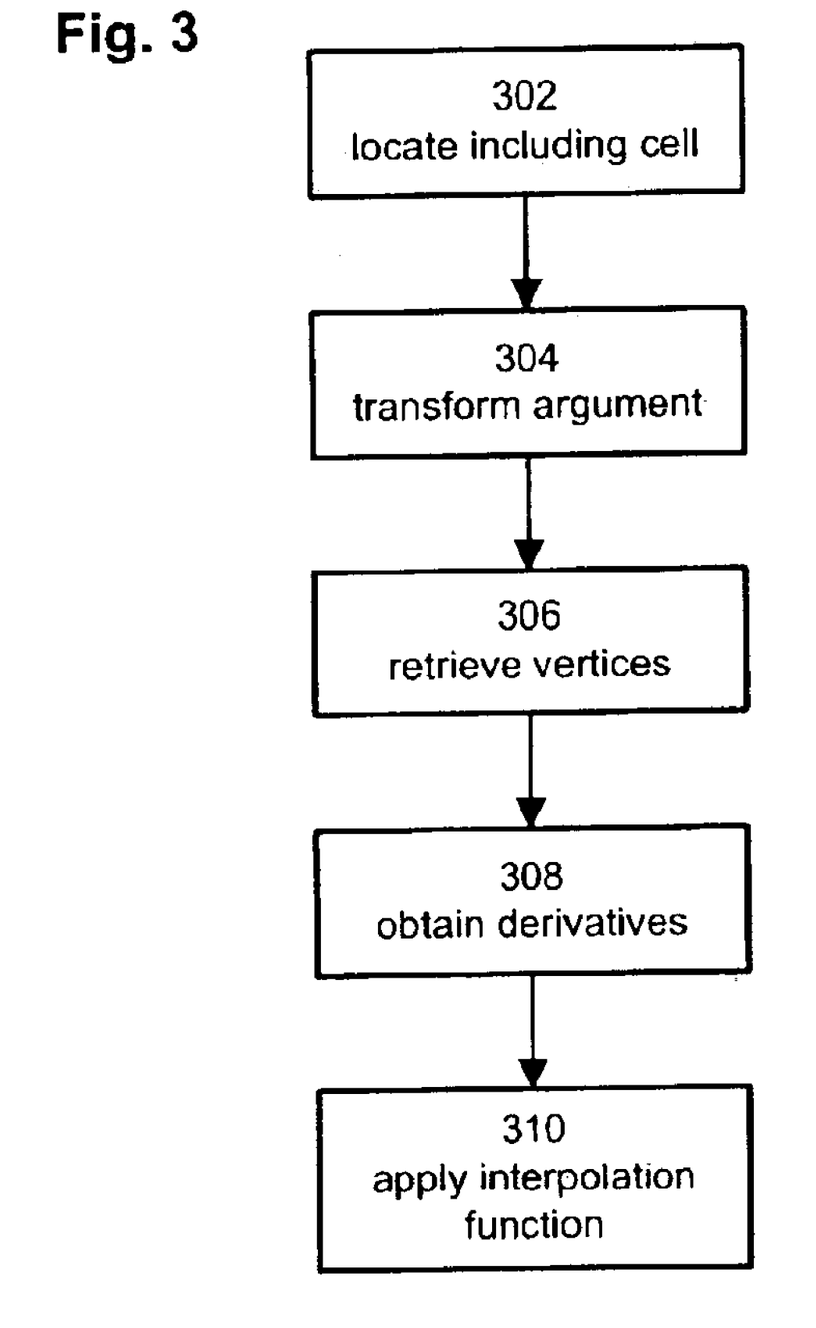
FIG. 3 is a flowchart showing the steps associated with a representative embodiment of the interpolation method provided by the present invention.

As described previously, the reduced multicubic interpolation is typically used to interpolate a function Y[X] where X (in the scatterometry case) is typically a vector or matrix that includes computed reflectance quantities such as complex reflectance corresponding to multiple wavelengths, incidence angles, and polarization states. As shown in FIG. 3, interpolation of X begins by locating an interpolation cell m in which X is included (see step 302). The interpolation cell m is N-dimensional and includes X in each dimension (i.e., $X_j^{(m_j)} \leq X_j \leq X_j^{(m_j+1)}$; $m_j=0 \ldots M_j-1$; $j=1 \ldots N$).

In step 304, the interpolation argument X is mapped into a transformed argument x. The transformation is equivalent to moving the interpolation cell m to a unit cell with its base vertex at the origin. The transformed X argument, denoted $x=(x_1, x_2 \ldots x_N)$, is defined by:

$$x_j = \frac{X_j - X_j^{(m_j)}}{X_j^{(m_j+1)} - X_j^{(m_j)}}; \quad j = 1 \ldots N$$

Once X has been transformed, the problem of interpolating Y becomes a problem of interpolating a function y within the unit cell. In step 306, the values for y at each vertex of the unit cell are retrieved from the database. For the one dimensional case described above, this means that y[0] and y[1] are retrieved. For the two dimensional case, four y values would be retrieved: y[0,0], y[0,1], y[1,0] and y[1,1].

In step 308, first order derivatives are obtained for y at each vertex. For the one dimensional case described above, this means obtaining $\partial y[0]$ and $\partial y[1]$. Some implementations store the first derivatives as part of the interpolation database. In these cases, obtaining the first order derivatives is performed by database lookup. In other implementations, the first order derivatives are not stored and must be generated on-the-fly. Typically, this will involve a numerical method for estimating derivatives using the y at each vertex of the unit cell as well as nearby y values (e.g., y[−1] and y[2] for the one dimensional case).

In step 310, the interpolation function is evaluated using the y values and their associated first order derivatives.

Reduced-Cubic Interpolation with Finite-Difference Derivatives

In practice, the derivative terms $\partial_i y[s]$ in Equations 16 and 17 may not be readily available and must be evaluated by finite differencing. In these cases, the present invention provides a finite difference approach to reduced-cubic interpolation. For this approach, the gird-sampled function values y[s] are used for derivative estimation. Assuming that the sampling grid is uniform in each dimension (i.e., $X_j^{(m_j+1)} - X_j^{(m_j)}$ is the same for all $m_j=0 \ldots M_j-1$), a simple centered finite differencing approximation can be used:

$$\partial_i y[s] \cong \frac{1}{2}(y[s + e_i] - y[s - e_i]) \quad (19)$$

wherein $e_i$ is the unit vector:

$$e_i = (e_{i,1}, e_{i,2}, \ldots, e_{i,N}); \quad e_{i,j} = \begin{cases} 1, & i = j \\ 0, & i \neq j; \end{cases} \quad i, j = 1 \ldots N \quad (20)$$

If grid cell m is at the boundary of the data sampling range (i.e., $m_i=0$ or $m_i=M_i-1$ for some $i=1 \ldots N$), then one of the terms $y[s \pm e_i]$ in Equation 19 will be outside the sampling range. In this case a one-sided derivative estimator may be used:

$$\partial_i y[s] \cong \pm\left(-\frac{1}{2}y[s \pm 2e_i] + 2y[s \pm e_i] - \frac{3}{2}y[s]\right) \quad (21)$$

However, Equation 21 is less accurate than Equation 19, so the data sampling range should preferably be "padded" with data points external to the interpolation range to avoid the need for one-sided derivative estimators. (The padded sampling range should be defined such that for each grid point $X^{(m)}$ in the interpolation range, all points $X^{(m \pm e_i)}$ for $i=1 \ldots N$ are sampled.)

A higher-order derivative estimator may be used to improve interpolation accuracy:

$$\partial_i y[s] \cong \frac{2}{3}(y[s+e_i] - y[s-e_i]) - \frac{1}{12}(y[s+2e_i] - y[s-2e_i]) \quad (22)$$

For grid cells at or near the sampling boundary, higher-order, asymmetric derivative estimators such as the following may be employed (but at the expense of compromised accuracy), $$\partial_i y[s] \cong \pm \begin{pmatrix} -\frac{1}{4}y[s \mp e_i] - \frac{5}{6}y[s] + \\ \frac{3}{2}y[s \pm e_i] - \frac{1}{2}y[s \pm 2e_i] + \frac{1}{12}y[s \pm 3e_i] \end{pmatrix} \quad (23)$$

$$\partial_i y[s] \cong \pm \left( -\frac{1}{3}y[s \mp e_i] - \frac{1}{2}y[s] + y[s \pm e_i] - \frac{1}{6}y[s \pm 2e_i] \right) \quad (24)$$

$$\partial_i y[s] \cong \pm \begin{pmatrix} -\frac{25}{12}y[s] + 4y[s \pm e_i] - \\ 3y[s \pm 2e_i] + \frac{4}{3}y[s \pm 3e_i] - \frac{1}{4}y[s \pm 4e_i] \end{pmatrix} \quad (25)$$

$$\partial_i y[s] \cong \pm \begin{pmatrix} -\frac{11}{6}y[s] + 3y[s \pm e_i] - \\ \frac{3}{2}y[s \pm 2e_i] + \frac{1}{3}y[s \pm 3e_i] \end{pmatrix} \quad (26)$$

The need for these asymmetric derivative estimators can be avoided by padding the sampling range such that for each grid point $X^{(m)}$ in the interpolation range, all points $X^{(m \pm e_i)}$ and $X^{(m \pm 2e_i)}$ for i=1 ... N are sampled.

Reduced-Cubic Interpolation with Point Matching

With this method, the function matching conditions are similar to Equations 16 except that finite differences are substituted for the derivative terms:

$$y_I[s] = y[s], \quad (27)$$

$$\frac{1}{2}(y_I[s+e_i] - y_I[s-e_i]) = \frac{1}{2}(y[s+e_i] - y[s-e_i]);$$

$$s_j = 0, 1; \quad i, j = 1 \ldots N$$

The interpolation function is:

$$y_I[x] = \sum_{s: s_j = 0, 1 (j=1,\ldots N)} \left( u_s[x] y[s] + \sum_{i=1 \ldots N} v_{i,s}[x] \frac{1}{2}(y[s+e_i] - y[s-e_i]) \right) \quad (28)$$

The interpolation basis functions, $u_s[x]$ and $v_{i,s}[x]$, are defined by:

$$u_s[x] = \left( \prod_{j=1 \ldots N} (1 - x'_j) \right) \left( 1 + \frac{1}{3} \sum_{j=1 \ldots N} x'_j (1 - 2x'_j) \right) \quad (29)$$

$$v_{i,s}[x] = \frac{1}{3}(-1)^{s_i} \left( \prod_{j=1 \ldots N} (1 - x'_j) \right) x'_i (2 - x'_i)$$

and $x'_j$ is defined as:

$$x'_j = \begin{cases} x_j, & s_j = 0 \\ 1 - x_j, & s_j = 1. \end{cases}$$

If grid cell m is at the boundary of the data sampling range, Equation 28 is not applicable because it uses y data points outside the sampling range. In this case, the interpolation function may be defined by simply extrapolating from the nearest interior grid cell. However, if more than one of the $X_j$ coordinates is at the sampling limit the extrapolated function may not actually fit all the boundary points; and in any case, accuracy will be compromised in the boundary cells. Thus the data sampling range should preferably be padded to avoid the need for extrapolation.

Implementation Approach

The primary difficulty encountered in implementing the above algorithms is in translating the multidimensional array notation into conventional programming language syntax. For example, the data samples $Y[X^{(m)}]$ could be represented in Fortran by multidimensional array elements Ysample (m(1),m(2), ... m(N)), wherein m(j)=$m_j$. (If Y is a vector or matrix, the Ysample elements could be pointers to Y data structures.) However, this approach is very constraining because the number of array dimensions (N) must be a compile-time constant and cannot exceed seven (due to an inherent Fortran limitation). In C++, multidimensional arrays are represented by nested pointer indirection, e.g., Ysample[m[0]][m[1]] ... [m[N-1]], wherein m(j)=$m_{j+1}$. But this approach is also impractical because the number of dimensions is predetermined by the Ysample data type and the multiple pointer indirections are computationally inefficient.

A more practical approach is to represent all multidimensional arrays computationally as one-dimensional arrays, using a Fortran-style memory layout, and perform the array indexing operations manually. For example, the datum $Y[X^{(m)}]$ would be represented computationally as $$Y[X^{(m)}] = Y\text{sample}[m\_\text{index}] \quad (30)$$

wherein m_index is a scalar array index, which is a linear function of m:

$$m\_\text{index} = \text{offset} + \text{stride}[0]*m[0] + \text{stride}[1]*m[1] + \ldots \text{stride}[N-1]*m[N-1] \quad (31)$$

$$m(j) = m_{j+1} \quad (32)$$

The program logic, as well as the data structures, can be adapted for variable N. For example, following is a multidimensional array initialization routine using a conventional C++ array representation, $$\text{for } (m[N-1] = \text{extent}[N-1]; --m[N-1] >= 0;) \quad (33)$$

...

for (m[1] = extent[1]; --m[1] >= 0;)

for (m[0] = extent[0]; --m[0] >= 0;)

Ysample [m[0]] [m[1]] ... [m[N-1]] = ... ;

(Following Fortran nomenclature, the "extent" array represents the dimension extents.) This code structure is not applicable to variable N, but with the Equation 30 representation the multidimensional iteration can be implemented as follows for variable N,

```
bool done = false;
int m_index = offset;
for (int i = 0; i < N; ++i) {
    if (extent [i] == 0) {
        done = true;
        break;
    }
}
```

-continued

```
        m[i] = extent[i]-1;
        m_index += stride[i]*m[i];
    }
    while (!done) {
        Ysample[m_index] = ...;
        done = true;
        for (int i = 0; i < N; ++i) {
            if (--m[i] >= 0) {
                m_index -= stride[i];
                done = false;
                break;
            }
            m[i] = extent[i]-1;
            m_index += stride[i]*m[i];
        }
    }
```

Comparative Computational Performance

In each of the interpolation algorithms the interpolation function $y_1[x]$ is represented as a linear combination of the grid-sampled y values and (possibly) derivatives $\partial_i y$, wherein the linear coefficients are the x-dependent interpolation basis functions. Typically, y is a large data structure and the computational overhead associated with calculating the basis functions (Equation 10, 14, 18, or 29) is dominated by the computation of the linear combination (Equation 9, 13, 17, or 28). In this case the computation runtime is approximately proportional to the number of summation terms in the linear combination. For multilinear interpolation (Equation 9), the number of summation terms is $2^N$. For full multicubic interpolation (Equation 14) the number is $4^N$, and for reduced-cubic interpolation (Equation 17) it is $(1+N)2^N$. Thus, for large N the reduced-cubic interpolation has a very substantial efficiency advantage over full multicubic interpolation.

The reduced-cubic interpolation algorithm with point matching (Equation 28) has $(1+2N)2^N$ summation terms, as written. However, there are only $(1+N)2^N$ distinct y sample values appearing in Equation 28, so in practice this equation can be reformulated so that it also has $(1+N)2^N$ terms. This same condition also applies to Equation 17 with substitution of finite-difference derivatives, Equation 19. If the higher-order derivative estimator, Equation 22, is used in Equation 17, then the number of y samples per interpolation is $(1+2N)2^N$.

Continuity and Smoothness

Multilinear interpolation yields a global interpolation function $Y_1[X]$ that is continuous across grid cell boundaries, but which is not generally smooth (i.e., continuously differentiable). With full, multicubic interpolation, $Y_1[X]$ is globally continuous and smooth. The reduced-cubic interpolation function is globally continuous. It is not generally smooth across grid cell boundaries, although it is smooth at the grid points $X^{(m)}$. The same condition holds when finite-difference derivatives are used, although in this case the derivatives $\partial_i Y_1$ will not exactly match $\partial_i Y$ at the grid points. Reduced-cubic interpolation with point matching yields an interpolation function that is globally continuous but is not generally globally smooth (even at the grid points).

Interpolation Accuracy

In characterizing interpolation accuracy, it is useful to consider a function y[x] represented by a Taylor series near x=0, $$y[x] = \sum_{p: p_j=0 \ldots \infty (j=1 \ldots N)} \left( \left( \prod_{j=1 \ldots N} \frac{1}{p_j!} \partial_j^{p_j} \right) y[0] \prod_{j=1 \ldots N} (x_j)^{p_j} \right) \quad (35)$$

wherein $p=(p_1, p_2, \ldots p_N)$ and $0=(0,0, \ldots 0)$. Each monomial term $$\prod_j (x_j)^{p_j}$$

in Equation 35 has an associated "monomial order" $\Sigma p$ defined by $$\Sigma p = \sum_{j=1 \ldots N} p_j \quad (36)$$

"Interpolation accuracy order" is defined as the largest integer n such that any monomial of order n or less has zero contribution to the interpolation error:

$y_1[x]-y[x]$.

The accuracy order is related to the scaling relationship between the interpolation error and the grid sampling density. Suppose that the interpolation sampling interval sizes are all proportional to a common scaling factor $\epsilon$:

$$X_j^{(m_j+1)} - X_j^{(m_j)} = \epsilon \Delta_j^{(m_j)}; \; m_j = 0 \ldots M_j-1; \; j=1 \ldots N \quad (37)$$

Then, based on Equations 7 and 37, each $\partial_j$ term in Equation 35 carries with it an implicit factor of $\epsilon$, and each monomial term $$\prod_j (x_j)^{p_j}$$

has an implicit factor of $\epsilon^{\Sigma p}$ multiplying it. Thus, the lowest power of $\epsilon$ appearing in the interpolation error $y_1[x]-y[x]$ (represented as a Taylor series in $\epsilon$) will be $\epsilon^{n+1}$, wherein n is the interpolation accuracy order.

Multilinear interpolation (Equation 9) has accuracy order one. Multicubic interpolation (Equation 13) and reduced-cubic interpolation (Equation 17) both have accuracy order three. If the finite-difference approximation of either Equation 19 or 21 is employed in Equation 17 the accuracy order is reduced to two; however any of the higher-order derivative estimators, Equations 22–26, preserves order-three accuracy. Reduced-cubic interpolation with point matching also has order-three accuracy.

Following are lowest-order approximations for the interpolation error, for each interpolation algorithm.

Multilinear interpolation, Equations 9, 10:

$$y_I[x] - y[x] \cong \frac{1}{2} \sum_{i=1 \ldots N} \partial_i^2 y[0] x_i (1 - x_i) \quad (37)$$

Multicubic interpolation, Equations 13, 14:

$$y_I[x] - y[x] \cong -\frac{1}{24} \sum_{i=1 \ldots N} \partial_i^4 y[0] (x_i)^2 (1 - x_i)^2 \quad (38)$$

Reduced-cubic interpolation, Equations 17, 18:

$$y_I[x] - y[x] \cong -\frac{1}{24} \sum_{i=1 \ldots N} \partial_i^4 y[0] (x_i)^2 (1-x_i)^2 - \qquad (39)$$

$$\frac{1}{4} \sum_{j=2 \ldots N} \sum_{i=1 \ldots j-1} \partial_i^2 \partial_j^2 y[0] x_i(1-x_i)x_j(1-x_j)$$

Equations 17, 18 with the finite-difference derivative, Equation 19, substituted in Equation 17:

$$y_I[x] - y[x] \cong \frac{1}{6} \sum_{i=1 \ldots N} \partial_i^3 y[0] x_i(1-x_i)(1-2x_i) \qquad (40)$$

Equations 17, 18 with a higher-order finite-difference derivative, Equation 22: same as Equation 40.

Reduced-cubic interpolation with point matching, Equations 28, 29:

$$y_I[x] - y[x] \cong -\frac{1}{24} \sum_{i=1 \ldots N} \partial_i^4 y[0] (1+x_i)x_i(1-x_i)(2-x_i) - \qquad (42)$$

$$\frac{1}{4} \sum_{j=2 \ldots N} \sum_{i=1 \ldots j-1} \partial_i^2 \partial_j^2 y[0] x_i(1-x_i)x_j(1-x_j)$$

[Note: Equations 40 and 42 have a similar form; but the factor $(x_i)^2(1-x_i)^2$ multiplying $\partial_i^4 y[0]$ in Equation 40 takes on a maximum value of $\frac{1}{16}$ over the unit interval $0 \leq x_i \leq 1$, whereas the corresponding factor $(1+x_i)x_i(1-x_i)(2-x_i)$ in Equation 42 takes on a maximum value of $\frac{9}{16}$.

Thus, the accuracy of the point-matching method is an order of magnitude worse than the method employing accurate derivatives.]

The above error estimates do not consider the case where asymmetric derivative estimators (Equations 21, 23–26) are used. However, it is evident from the following lowest-order estimates of the derivative estimators that a significant accuracy penalty is incurred by using asymmetric estimators:

Equation (19):

$$\frac{1}{2}(y[s+e_i] - y[s-e_i]) - \partial_i y[s] \cong \frac{1}{6}\partial_i^3 y[s] \qquad (43)$$

Equation (21):

$$\pm\left(-\frac{1}{2}y[s \pm 2e_i] + 2y[s \pm e_i] - \frac{3}{2}y[s]\right) - \partial_i y[s] \cong -\frac{1}{3}\partial_i^3 y[s] \qquad (44)$$

Equation (22):

$$\frac{2}{3}(y[s+e_i] - y[s-e_i]) - \frac{1}{12}(y[s+2e_i] - y[s-2e_i]) - \partial_i y[s] \cong -\frac{1}{30}\partial_i^5 y[s] \qquad (45)$$

Equation (23):

$$\pm\left(-\frac{1}{4}y[s \mp e_i] - \frac{5}{6}y[s] + \frac{3}{2}y[s \pm e_i] - \frac{1}{2}y[s \pm 2e_i] + \frac{1}{12}y[s \pm 3e_i]\right) - \qquad (46)$$

$$\partial_i y[s] \cong \frac{1}{20}\partial_i^5 y[s]$$

Equation (24):

$$\pm\left(-\frac{1}{3}y[s \mp e_i] - \frac{1}{2}y[s] + y[s \pm e_i] - \frac{1}{6}y[s \pm 2e_i]\right) - \partial_i y[s] \cong \qquad (47)$$

$$\mp \frac{1}{12}\partial_i^4 y[s]$$

Equation (25):

$$\pm\left(-\frac{25}{12}y[s] + 4y[s \pm e_i] - 3y[s \pm 2e_i] + \frac{4}{3}y[s \pm 3e_i] - \frac{1}{4}y[s \pm 4e_i]\right) - \qquad (48)$$

$$\partial_i y[s] \cong -\frac{1}{5}\partial_i^5 y[s]$$

Equation (26):

$$\pm\left(-\frac{11}{6}y[s] + 3y[s \pm e_i] - \frac{3}{2}y[s \pm 2e_i] + \frac{1}{3}y[s \pm 3e_i]\right) - \partial_i y[s] \cong \qquad (49)$$

$$\pm \frac{1}{4}\partial_i^4 y[s]$$

Discussion

The multilinear and multicubic interpolation functions (Equations 9 and 13) are obtained by applying one-dimensional interpolation in each dimension separately. For example, applying linear interpolation successively to $x_1$, $x_2$, ... $x_N$, yields a multilinear interpolation function of the form $$y[x] \cong y_I[x] = \sum_{p: p_j=0,1(j=1 \ldots N)} a_p \prod_{j=1 \ldots N} (x_j)^{p_j} \qquad (50)$$

wherein the $2^N$ coefficients $a_p$ are determined from the corresponding $2^N$ point-matching conditions, Equation 8. Substituting $y_I[x]$ from Equation 50 into Equation 8, yields a set of $2^N$ equations that can be solved for the $a_p$ coefficients. $a_p$ will evidently be a linear combination of the constraint values $y[s]$ appearing in Equation 8; hence substitution of the solution in Equation 50 yields a expression for $y_I[x]$ as a linear combination of the $y[s]$ constraints, as expressed in Equation 9; wherein the $u_s[x]$ terms are multilinear functions of x comprising the same monomial terms appearing in Equation 50.

Rather than solving for the $a_p$ coefficients explicitly, the basis functions $u_s[x]$ are obtained by direct substitution of Equation 9 into Equation 8 (with x=s'), $$\sum_{s: s_j=0,1(j=1 \ldots N)} u_s[s']y[s] = y[s']; \quad s'_j = 0, 1; \quad j = 1 \ldots N \qquad (51)$$

This applies to any function y; hence the basis functions satisfy the condition $$u_s[s'] = \begin{cases} 1, & s = s' \\ 0 & s \neq s'; \ s_j, s'_j = 0, 1; \ j = 1 \ldots N \end{cases} \qquad (52)$$

$u_s[x]$ is a $2^N$-term multilinear function (similar to Equation 50) whose coefficients are determined by the $2^N$ conditions defined by Equation 52. (There are $2^N$ distinct s' values in Equation 52.) Based on the symmetry of Equation 52, the following condition holds for any j=1 ... N:

$$u_s[x]|_{s_j \leftarrow 1-s_j} = u_s[x]|_{x_j \leftarrow 1-x_j} \qquad (53)$$

Thus, it suffices to consider the case s=0. Given the basis function $u_0[x]$, Equation 53 can be applied to obtain $u_s[x]$ for any s ($s_j$=0,1; j=1 . . . N). Assuming multiplicative separability of $u_0[x]$ in $x_1, x_2, \ldots x_N$, the following result is readily obtained from Equation 52:

$$u_0[x] = \prod_{j=1 \ldots N} (1 - x_j) \tag{54}$$

and application of Equation 53 yields the result, Equation 10.

The methodology outlined above can also be applied to multicubic interpolation. In this case, the interpolation function has a form similar to Equation 50, except that $p_j$ ranges from 0 to 3:

$$y[x] \cong y_I[x] = \sum_{p: p_j = 0 \ldots 3 (j=1 \ldots N)} a_p \prod_{j=1 \ldots N} (x_j)^{p_j} \tag{55}$$

This expression, together with the constraints defined by Equation 12, implies an interpolation function having the form of Equation 13 wherein the basis functions $u_{k,s}[x]$ comprise the same monomials appearing in Equation 54. The defining conditions for $u_{k,s}[x]$ are $$\prod_{j=1 \ldots N} \partial_j^{k'_j} u_{k,s}[s'] = \begin{cases} 1, & k' = k \text{ and } s' = s \\ 0, & k' \neq k \text{ or } s' \neq s; \end{cases} \tag{56}$$

$$k'_j, k_j, s'_j, s_j = 0, 1; \quad j = 1 \ldots N$$

The basis functions satisfy the symmetry conditions, $$u_{k,s}[x]|_{s_j \leftarrow 1-s_j} = (-1)^{k_j} u_{k,s}[x]|_{x_j \leftarrow 1-x_j} \tag{57}$$

Hence, given the basis functions $u_{k,0}[x]$, all the other basis functions can be determined by application of Equation 57. Assuming multiplicative separability of $u_{k,0}[x]$ in $x_1, x_2, \ldots x_N$, yields:

$$u_{k,0}[x] = \prod_{j=1 \ldots N} f_{k_j}[x_j] \tag{58}$$

wherein $f$ is defined by Equation 15; and application of Equation 57 then yields Equation 14.

The starting point for reduced-cubic interpolation is the constraint conditions, Equations 16, which involve first derivative matching but do not involve the mixed first derivatives appearing in Equation 12. Since equation 16 defines $(1+N)2^N$ constraints, an interpolation function is needed that has this same number of free parameters. The following functional form meets this criterion:

$$y_I[x] = \sum_{p: p_j = 0, 1 (j=1 \ldots N)} \left( \left( a_p + \sum_{j=1 \ldots N} b_{j,p}(x_j)^2 \right) \prod_{j=1 \ldots N} (x_j)^{p_j} \right) \tag{59}$$

Equations 16 and 59 imply that $y_I[x]$ can be represented as a linear combination of the constraint values $y[s]$ and $\partial_i y[s]$, as represented in Equation 17; wherein the basis functions $u_s[x]$ and $v_{i,s}[x]$ comprise the same monomials that appear in Equation 59.

After back-substituting Equation 17 in Equation 16 and matching corresponding constraint coefficients, the following defining conditions for $u_s[x]$ and $v_{i,s}[x]$ are obtained, $$u_s[s'] = \begin{cases} 1, & s' = s \\ 0, & s' \neq s \end{cases} \tag{60}$$

$$v_{i,s}[s'] = 0$$

$$\partial_{i'} u_s[s'] = 0$$

$$\partial_{i'} v_{i,s}[s'] = \begin{cases} 1, & i' = i \text{ and } s' = s \\ 0, & i' \neq i \text{ or } s' \neq s \end{cases}$$

$$s'_j, s_j = 0, 1; \quad i', i, j = 1 \ldots N$$

The basis functions satisfy the following symmetry relationships, $$u_s[x]|_{s_j \to 1-s_j} = u_s[x]|_{x_j \to 1-x_j} \tag{61}$$

$$v_{i,s}[x]|_{s_j \to 1-s_j} = \begin{cases} v_{i,s}[x]|_{x_j \to 1-x'_j} & i = j \\ -v_{i,s}[x]|_{x_j \to 1-x'_j} & i \neq j \end{cases}$$

The following functions satisfy Equation 60 with s=0, $$u_0[x] = \left( \prod_{j=1 \ldots N} (1 - x_j) \right) \left( 1 + \sum_{j=1 \ldots N} x_j(1 - 2x_j) \right) \tag{62}$$

$$v_{i,0}[x] = \left( \prod_{j=1 \ldots N} (1 - x_j) \right) x_i(1 - x_i)$$

and applying Equations 61, 18 are obtained.

Global continuity of $Y_I[X]$ can be demonstrated for multilinear interpolation as follows: If Equation 9 is evaluated on one of the interpolation cell's hyperplane boundaries, e.g. at $x_1=0$, then the computed value $y_I[x]$ will depend only on $y[s]$ values sampled in the hyperplane (i.e., with $s_1=0$). Hence the untransformed interpolation function $Y_1^{(m)}[X]$ evaluated on the hyperplane $X_1=X_1^{(m_1)}$ (on the boundary of cell m), will depend only on $Y[X]$ values sampled in the hyperplane. Another interpolation function $Y_1^{(m-e_1)}[X]$ defined on adjacent cell $m-e_1$, will similarly have a functional form in the hyperplane $X_1=X_1^{(m_1)}$ that is defined entirely by the same $Y[X]$ values; hence the two functions $Y_1^{(m)}[X]$ and $Y_1^{(m-e_1)}[X]$ will be matched at the common boundary between cell m and cell $m-e_1$. The same condition applies to all bounding hyperplanes between interpolation cells; hence the global interpolation function $Y_I[X]$ is everywhere continuous.

The above line of reasoning can be extended to show that all of the interpolation algorithms outlined in Section 3 yield globally continuous interpolation functions, and that multicubic interpolation yields an interpolation function that is also globally smooth. The reduced-cubic interpolation function, Equation 17, is not globally smooth; but it is smooth at the grid points because the function derivatives are constrained by Equation 16 to be matched between adjacent grid cells.

Assuming that no approximations are made in the interpolation constraints, the interpolation error $y_I[x]-y[x]$ will be identically zero (by construction) when $y[x]$ is any polynomial comprising the same monomial terms that are in $y_I[x]$. Thus, to determine an error estimate, it is appropriate to limit consideration to the lowest-order monomial terms in $y[x]$ that are not in $y_I[x]$. For example, the multilinear function $y_1[x]$ defined by Equation 50 includes all monomials up to order 1; thus the multilinear interpolation error is dominated by monomials of order 2 that are not in the multilinear expansion. There are N such monomials: $(x_j)^2$, $j=1 \ldots N$. Considering, for example, the monomial function $$y[x]=(x_1)^2 \quad (63a)$$

the terms $y[s]$ in Equation 9 are $$y[s] = \begin{cases} 0, & s_1 = 0 \\ 1, & s_1 = 1 \end{cases} \quad (63b)$$

With this substitution, Equation 9 reduces to $y_1[x]=x_1$, $$y_l[x] = \sum_{s:s_1=1;s_j=0,1(j=2\ldots N)} u_s[x] = \sum_{s_2=0,1} \cdots \sum_{s_N=0,1} u_{(1,s_2,\ldots s_N)}[x] \quad (63c)$$

$$= \sum_{s_2=0,1} \cdots \sum_{s_N=0,1} x_1 \prod_{j=2\ldots N} (1-x'_j) = x_1 \prod_{j=2\ldots N} \sum_{s_j=0,1} (1-x'_j)$$

$$= x_1 \prod_{j=2\ldots N} ((1-x_j)+x_j) = x_1$$

The interpolation error, for $y[x]$ defined by Equation 63a, is $$y_1[x]-y[x]=x_1(1-x_1) \quad (63d)$$

Generalizing this to an arbitrary function $y[x]$ defined by a Taylor series (Equation 35), the lowest-order interpolation error for multilinear interpolation is given by Equation 38.

A similar procedure yields the interpolation error estimates for multicubic interpolation (Equation 39), reduced-cubic interpolation with exact derivatives (Equation 40), and reduced-cubic interpolation with point matching (Equation 42). Each of these methods has the property that the interpolation error is zero for any monomial included in $y_1[x]$. For example, in the case of multicubic interpolation, the interpolation function $y_1[x]$ defined by Equation 55 includes all monomials of order 3 or less, and the only order-4 monomials not included in the multicubic expansion are $(x_j)^4$, $j=1 \ldots N$. Thus the multicubic interpolation error, Equation 39, can be estimated by considering the special case $y[x]=(x_1)^4$ (analogous to Equation 63a). The reduced-cubic expansion, Equation 59, also includes all monomials of order 3 or less, but the order-4 monomials not included in Equation 59 include the functions $(x_j)^4$ and also $(x_i)^2(x_j)^2$; $i \neq j$. Functions $y[x]$ of both forms must be considered in deriving Equations 40 and 42.

Equation 41 is a special case because the interpolation algorithm relies on an additional approximation, the derivative estimate (Equation 19), which is only accurate to order 2. (In this case, the $y_1$ derivatives are only constrained to match finite-difference y derivatives at the grid points.) The lowest-order monomials for which Equation 19 is in error are: $(x_j)^3$, $j=1 \ldots N$; thus the interpolation error estimate in Equation 41 is determined by considering functions $y[x]$ of this form. However, if the higher-order derivative estimator, Equation 22, is used, the accuracy estimate in Equation 40 is unchanged because Equation 22 has accuracy order 4 (see Equation 45).

Comparison

The primary advantages and disadvantages of the interpolation algorithms considered above are summarized as follows:

The prior art multilinear interpolation (Equation 9) is the most computationally efficient algorithm, requiring $2^N$ summation terms per interpolation. The interpolation function is globally continuous, but is generally not smooth at the grid cell boundaries. Multilinear interpolation only has accuracy order 1 (Equation 38).

Full, multicubic interpolation (Equation 13) (also prior art) has accuracy order 3 (Equation 39). (This assumes accurate derivatives are used.) The multicubic interpolation function is globally continuous and smooth. However, the algorithm is very inefficient, requiring $4^N$ summation terms.

Reduced-cubic interpolation with exact derivatives (Equation 17) also has accuracy order 3 (Equation 40), but requires only $(1+N)2^N$ summation terms. The interpolation function is globally continuous. It is not generally smooth, except at the grid points. A disadvantage of this method (as well as the multicubic interpolation method considered here) is that it requires derivative information.

The need for exact derivatives can be eliminated by using finite-difference derivatives, but there are tradeoffs. If a simple, centered-difference derivative estimator (Equation 19) is used, the interpolation accuracy is reduced to order 2 (Equation 41). A higher-order derivative estimator (Equation 22) may be used to restore order-3 accuracy, but then the number of summation terms is increased to: $(1+2N)2^N$.

The above tradeoff can be circumvented by using the reduced-cubic interpolation method with point matching (Equation 28). This method does not require derivatives; it has accuracy order 3 (Equation 42); and the required number of summation terms is $(1+N)2^N$. However, the accuracy error is typically much larger (e.g., by an order of magnitude) than that of the derivative-matching methods (assuming that accurate derivatives are used). Another possible disadvantage is that the interpolation function may have poorer smoothness characteristics compared to the other reduced-cubic methods. (The point-matching interpolation function is generally not smooth between grid cells, even at the grid points.)

What is claimed is:

1. A method for optically inspecting a semiconductor wafer, the method comprising:
   generating a database consisting of a plurality of interpolation points, each interpolation point providing a mapping between a theoretical optical response characteristic for the semiconductor wafer and a corresponding set of N parameters with N being greater than 2;
   focusing a beam of radiation on the semiconductor wafer and measuring the resulting diffraction to generate an empirical optical response characteristic; and
   generating an interpolated optical response characteristic to match the empirical spectral response, where the interpolated optical response characteristic is calculated using a reduced multicubic function in which all derivative terms are simple, with the reduced multicubic function being substantially continuous and substantially matching the theoretical optical response characteristic at each interpolation point.

2. A method as recited in claim 1 where the total number of database quantities used to generate the interpolated optical response characteristic is less than $4^N$.

3. A method as recited in claim 1 where the total number of database quantities used to generate the interpolated optical response characteristic is $(1+N)2^N$.

4. A method as recited in claim 1 where the derivative terms in the reduced multicubic function are generated as finite difference approximations.

5. A method as recited in claim 1 where the derivative terms in the reduced multicubic function are retrieved from the database.

6. A method of evaluating a sample comprising;

generating a database consisting of a plurality of data points, each point defined by a parameter set consisting of specific parameter values and an associated optical characteristic function value sampled at the particular parameter set;

illuminating the sample with a probe beam and measuring the change induced in the probe beam resulting from the interaction with the sample and generating output signals in response thereto;

comparing the output signals with the points in the database using a fitting algorithm and interpolation model, wherein the interpolation model computes a substantially continuous interpolated optical characteristic function at specific interpolation parameter sets, and wherein the interpolation parameter sets are not limited to, but are computed from, those of the data points in the database, with the interpolated optical characteristic function substantially matching the optical response characteristic at each database point, said comparing being repeated until a best fit parameter set is identified as the measured parameter values of the sample;

where the number of database quantities used for the computation at each interpolation parameter set is less than $4^N$, where N is equal to the number of parameters; and where the interpolation accuracy order is higher than second-order.

7. A method as recited in claim 6 where the total number of database quantities used for the computation at each interpolation parameter set is $(1+N)2^N$.

8. A method for optically inspecting a semiconductor wafer, the method comprising:

focusing a beam of radiation on the semiconductor wafer and measuring the resulting diffraction to generate an empirical optical response characteristic;

interpolating a function Y[X] to generate a theoretical optical response characteristic, where X is a vector of N parameters with N being greater than 2, the interpolation process comprising:

locating an interpolation cell within a database of interpolation points, where each interpolation point is a mapping between a value for the function Y and a corresponding vector of N parameters, the interpolation cell including X on a dimension-by-dimension basis;

retrieving the interpolation points corresponding to each vertex of the interpolation cell; and using the retrieved interpolation points to evaluate a reduced multicubic function in which all derivative terms are simple.

9. A method as recited in claim 8 where the derivative terms in the reduced multicubic function are generated as finite difference approximations.

10. A method as recited in claim 9 where the derivative terms in the reduced multicubic function are retrieved from the database.

11. A method for optically inspecting a semiconductor wafer, the method comprising:

generating a database consisting of a plurality of interpolation points, each interpolation point providing a mapping between a theoretical optical response characteristic for the semiconductor wafer and a corresponding set of N parameters with N being greater than 2;

focusing a beam of radiation on the semiconductor wafer and measuring the resulting diffraction to generate an empirical optical response characteristic; and generating an interpolated optical response characteristic to match the empirical spectral response, where the interpolated optical response characteristic is calculated using a reduced multicubic with a polynomial function in which all derivative terms are simple, with the polynomial the reduced multicubic function being substantially continuous and substantially matching the theoretical optical response characteristic at each interpolation point.

12. A method as recited in claim 11 where the derivative terms in the reduced multicubic function are generated as finite difference approximations.

13. A method as recited in claim 12 where the derivative terms in the reduced multicubic function are retrieved from the database.

* * * * *